United States Patent [19]

Greinke

[11] Plant 4,244

[45] Apr. 25, 1978

[54] CHRYSANTHEMUM NAMED YELLOW JACKET

[75] Inventor: David Greinke, Bradenton, Fla.

[73] Assignee: Pan-American Plant Company, West Chicago, Ill.

[21] Appl. No.: 797,495

[22] Filed: May 16, 1977

[51] Int. Cl.[2] ..... A01H 5/00

[52] U.S. Cl. ..... Plt./75

[58] Field of Search ..... Plt./74–75

*Primary Examiner*—Robert E. Bagwill

*Attorney, Agent, or Firm*—Chas. W. Rummler

[57] ABSTRACT

A new variety of chrysanthemum plant, particularly suitable for outdoor garden culture and for use as a greenhouse pot plant, characterized by its numerous, small, bright yellow blooms which are of single flower form and produced in a relatively open spray formation. This new plant is also distinguished by its excellent performance as a late spring, summer and early fall potted plant and as a natural season garden plant; and by its short, compact plant habit which requires no growth retardants and has excellent breaking ability when manually pinched.

2 Drawing Figures

BACKGROUND OF THE NEW PLANT

My new variety of chrysanthemum plant was discovered by me in 1972 at Bradenton, Fla., as a seedling of unidentified parentage appearing among chrysanthemum plants cultured by me in the course of breeding efforts carried on by me with the object of developing new varieties for use as garden plants. The short and much branched growth of this plant and its many small but very attractive blooms caused me to select this plant for propagation and test, which I promptly did by cuttings from the original plant and found that its scions possessed all of its distinguishing features. Subsequent propagation of this new plant at Bradenton, Fla., by means of vegetative cuttings has demonstrated that the distinctive characteristics of this new chrysanthemum hold true from generation to generation and are firmly fixed. Commercial scale propagation of this new plant is now being carried on at Cortez, Fla., and at West Chicago, Ill.

DESCRIPTION OF THE DRAWINGS

This new chrysanthemum plant is illustrated by the accompanying drawings, the first of which is a photographic print in full color showing a potted plant of the new variety in full bloom with several stages of buds and flowers, the colors shown being as neary true as it is reasonably possible to obtain by conventional photographic procedures and the photograph being of a plant grown at West Chicago, Ill., and flowered in February, 1977.

The second sheet of drawings is a print of a mechanical photocopy of typical leaves of the new plant at several stages of maturity.

DESCRIPTION OF THE NEW PLANT

The following is a detailed description of my new chrysanthemum plant variety with the color designations according to the R.H.S. Colour Chart published by The Royal Horticultural Society of London, England, the observations having been made of plants propagated and grown at West Chicago, Ill.

THE PLANT

Origin: Seedling.

Parentage: Unknown, this plant having been found among random pollinated plants of a similar variety.

Classification:

*Botanic.*—*Chrysanthemum morifolium.*

*Commercial.*—Outdoor garden plant and greenhouse pot plant.

Form: Perennial herbaceous bush.

Height: 4½ to 7 inches as a pot plant, and 9 to 14 inches as an outdoor garden plant.

Growth: Terminal, with low spreading habit, sturdy with very good strength but relatively low vigor.

Branching: Very good under natural conditions.

Foliage:

*Quantity.*—Abundant, six to nine leaves per 3 inches of stem.

*Leaf size.*—About 1½ to 2½ inches long.

*Leaf shape.*—Lanceolate, lobed and deeply serrated.

*Surface texture.*—Canescent.

*Venation.*—Pinnately veined.

*Color.*—Upper side — Yellow Green 147A. Under side — Yellow Green 147B.

*Petioles.*—¼ to ⅞ inch long.

THE BUD

Form: Globular.

Size: 3/16 to ¼ inch in diameter. ⅛ to 3/16 inch in depth.

Opening: The bud opens slowly.

Color:

*When phyllaries first divide.*—Yellow Green 151B.

*When florets begin to unfurl.*—Yellow Orange 14A.

Phyllaries: Many, as involucral bracts borne on the outside of the receptacle.

*Form.*—Spear-shaped and upstanding.

*Color.*—Inside surface — Greyed Green 146B. Outside surface — Greyed Green 146A.

*Surface texture.*—Pubescent.

Peduncle:

*Length.*—¼ to 1⅜ inches.

*Surface texture.*—Pubescent.

*Strength.*—Erect and strong.

*Color.*—Yellow Green 147C.

THE FLOWER

Blooming capability: This plant can be flowered the year around with photoperiod control.

*Response.*—9 weeks.

*Recommended flowering.*—April 10 to November 1.

*Natural flowering season.*—About September 26 to October 9.

Blooms:

*Flower type.*—Composite and single.

*Size.*—Small. Diameter: About $\frac{7}{8}$ to 2 inches. Depth: $\frac{1}{4}$ to $\frac{5}{8}$ inch.

*Shape.*—Flat.

*Borne.*—Singly, as a head of many florets on a receptacle, in a relatively open spray formation.

*Florets.*—Numerous in number. Form: Linear, with obtuse apex. Arrangement: three or four rows of ray florets extending from the disc. Texture: Medium firm. Appearance: Very slight shine. Discoloration: None. There is no fading.

Color:

| Ray Florets: | March | October | November |
|---|---|---|---|
| Upper surface - | 9A | 14B | 9A |
| Reverse side - | 8A | 9B | 8A |

Disc florets: At center—144A; at perimeter—17A.

General color tonality of blooms: Yellow 9A when viewed from a distance of 6 feet.

Effect of weather: Blooms are not affected by hot or wet weather.

Persistence: Florets hang on and dry.

Fragrance: Typical chrysanthemum.

Lasting quality:

*On plant.*—3 weeks.

*As cut flower.*—Not recommended for cut flowers.

REPRODUCTIVE ORGANS

Stamens:

*Number.*—5.

*Arrangement.*—Syngenesious.

*Filaments.*—Length — About 1/16 to $\frac{1}{8}$ inch. Color: Light Yellow.

*Pollen.*—Color — Yellow.

Pistils:

*Number.*—One for each ray and disc floret.

*Styles.*—About $\frac{1}{8}$ to 3/16 inch long.

*Stigmas.*—Color — Yellow.

Ovaries: Inferior bicarpellate.

This new chrysanthemum plant is particularly characterized by its production of numerous, small, bright yellow blooms which are of single flower form and are displayed in a relatively open spray arrangement on a short, compact plant which has excellent performance as a late spring, summer and late fall 4 to 5 inch potted plant and as a natural season garden chrysanthemum. This plant has a 9-week photoperiod response, but with delayed flowering when grown under 62° F. It requires no growth retardants to maintain its low, compact habit and has excellent breaking ability when manually pinched, producing six to nine lateral breaks. It also has strong stems and abundant small to medium sized, dark green, glossy foliage which provides a very attractive overall appearance.

I claim:

1. A new and distinct chrysanthemum cultivar substantially as herein shown and described, characterized by its abundant production of small, bright yellow blooms which appear in single flower form in a relatively open spray formation on a short, compact plant which has excellent breaking ability and abundant medium sized, dark green and glossy foliage.

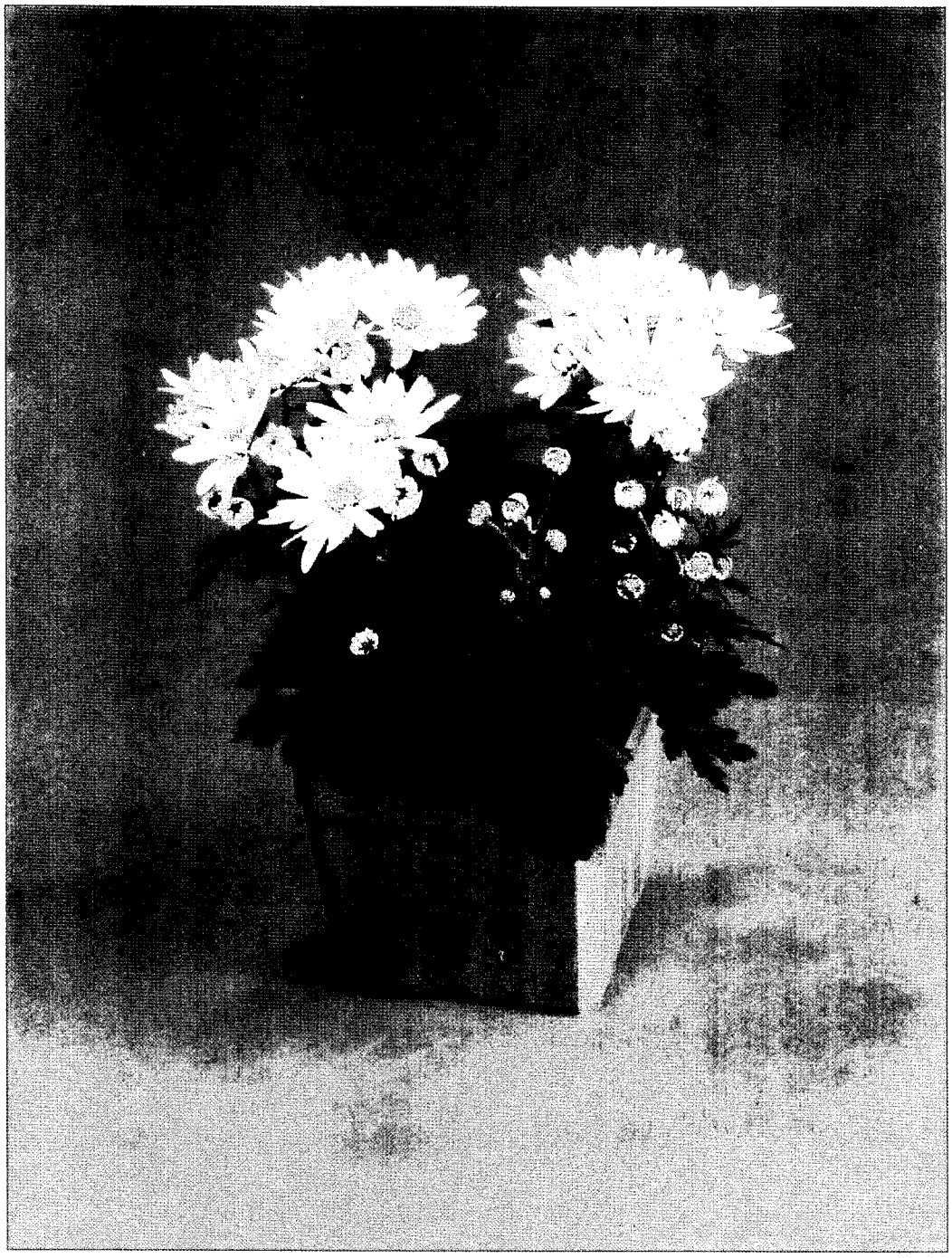

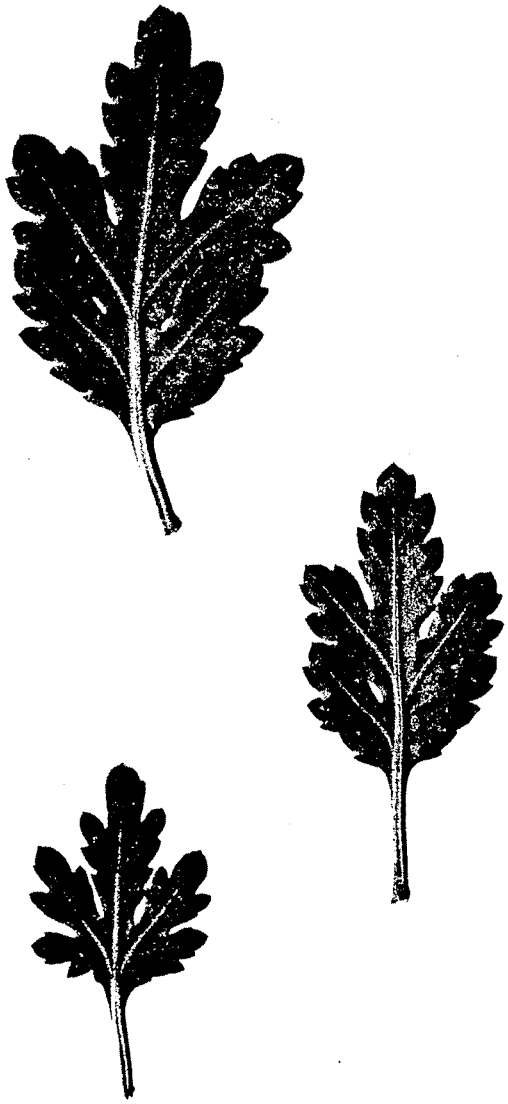

* * * * *